US007532935B2

(12) United States Patent
Maschino et al.

(10) Patent No.: US 7,532,935 B2
(45) Date of Patent: *May 12, 2009

(54) SELECTIVE NEUROSTIMULATION FOR TREATING MOOD DISORDERS

(75) Inventors: Steven E. Maschino, Seabrook, TX (US); William Buras, Friendswood, TX (US); Stephen Brannan, Friendswood, TX (US)

(73) Assignee: Cyberonics, Inc., Houston, TX (US)

( * ) Notice: Subject to any disclaimer, the term of this patent is extended or adjusted under 35 U.S.C. 154(b) by 521 days.

This patent is subject to a terminal disclaimer.

(21) Appl. No.: 11/193,121

(22) Filed: Jul. 29, 2005

(65) Prior Publication Data

US 2007/0027500 A1 Feb. 1, 2007

(51) Int. Cl.
*A61N 1/00* (2006.01)
(52) U.S. Cl. ....................................................... 607/45
(58) Field of Classification Search ..................... 607/2, 607/3, 45; 128/898
See application file for complete search history.

(56) References Cited

U.S. PATENT DOCUMENTS

| | | | |
|---|---|---|---|
| 3,796,221 A | 3/1974 | Hagfors | |
| 4,119,618 A | 10/1978 | Said | |
| 4,431,000 A | 2/1984 | Butler et al. | |
| 4,556,064 A | 12/1985 | Pomeranz et al. | |
| 4,702,254 A | 10/1987 | Zabara | |
| 4,745,923 A | 5/1988 | Winstrom | |
| 4,867,164 A | 9/1989 | Zabara | |
| 5,833,709 A * | 11/1998 | Rise et al. .................... 607/2 |
| 6,529,774 B1 | 3/2003 | Greene | |
| 6,532,388 B1 | 3/2003 | Hill et al. | |
| 6,549,804 B1 | 4/2003 | Osorio et al. | |
| 6,556,868 B2 | 4/2003 | Naritoku et al. | |
| 6,560,486 B1 | 5/2003 | Osorio et al. | |
| 6,564,102 B1 | 5/2003 | Boveja | |
| 6,587,727 B2 | 7/2003 | Osorio et al. | |
| 6,591,138 B1 | 7/2003 | Fischell et al. | |
| 6,594,524 B2 | 7/2003 | Esteller et al. | |
| 6,609,030 B1 | 8/2003 | Rezai et al. | |

(Continued)

FOREIGN PATENT DOCUMENTS

WO 2004000413 A2 12/2003

(Continued)

OTHER PUBLICATIONS

Andrews, P.L.R. et al, "A Protective Role for Vagal Afferents: An Hypothesis," Neuroanatomy and Physiology of Abdominal Vagal Afferents, Sue Ritter et al, eds., CRC Press, New York, NY, 1992, pp. 281-298.

(Continued)

*Primary Examiner*—George Manuel
(74) *Attorney, Agent, or Firm*—Conley Rose, P.C.; Timothy L. Scott

(57) ABSTRACT

A method and device for treating a mood and/or anxiety disorder are disclosed which comprise electrical, chemical or magnetic stimulation of certain areas of the brain to modulate neuronal activity of areas associated with symptoms of mood disorders. In certain embodiments, deep brain stimulation is combined with cranial nerve stimulation to enhance symptomatic relief of the disorder. Certain embodiments also employ a sensing capability to optimize the therapeutic treatment regimen.

30 Claims, 5 Drawing Sheets

U.S. PATENT DOCUMENTS

| | | | |
|---|---|---|---|
| 6,622,038 B2 | 9/2003 | Barrett et al. | |
| 6,622,047 B2 | 9/2003 | Barrett et al. | |
| 6,647,296 B2 | 11/2003 | Fischell et al. | |
| 6,671,555 B2 | 12/2003 | Gielen et al. | |
| 6,671,556 B2 | 12/2003 | Osorio et al. | |
| 6,690,974 B2 | 2/2004 | Archer et al. | |
| 6,708,064 B2 | 3/2004 | Rezai | |
| 6,721,603 B2 | 4/2004 | Zabara et al. | |
| 6,735,475 B1 | 5/2004 | Whitehurst et al. | |
| 6,760,626 B1 | 7/2004 | Boveja | |
| 6,788,975 B1 | 9/2004 | Whitehurst et al. | |
| 6,819,956 B2 | 11/2004 | DiLorenzo | |
| 6,819,958 B2 | 11/2004 | Weiner et al. | |
| 6,920,357 B2 | 7/2005 | Osorio et al. | |
| 6,944,501 B1 | 9/2005 | Pless | |
| 6,961,618 B2 | 11/2005 | Osorio et al. | |
| 7,006,872 B2 | 2/2006 | Gielen et al. | |
| 7,050,856 B2 | 5/2006 | Sypulkowski | |
| 7,054,686 B2 | 5/2006 | MacDonald | |
| 2002/0099412 A1 | 7/2002 | Fischell et al. | |
| 2002/0151939 A1 | 10/2002 | Rezai | |
| 2003/0181954 A1 | 9/2003 | Rezai | |
| 2004/0153129 A1 | 8/2004 | Pless et al. | |
| 2004/0172089 A1 | 9/2004 | Whitehurst et al. | |
| 2004/0172091 A1 | 9/2004 | Rezai | |
| 2004/0263172 A1 | 12/2004 | Gray et al. | |
| 2005/0004621 A1 | 1/2005 | Boveja et al. | |
| 2005/0021103 A1 | 1/2005 | DiLorenzo | |
| 2005/0021104 A1 | 1/2005 | DiLorenzo | |
| 2005/0049655 A1 | 3/2005 | Boveja et al. | |
| 2005/0065574 A1 | 3/2005 | Rezai | |
| 2005/0119703 A1 | 6/2005 | DiLorenzo | |
| 2005/0143786 A1 | 6/2005 | Boveja et al. | |
| 2005/0154425 A1 | 7/2005 | Boveja et al. | |
| 2005/0165458 A1 | 7/2005 | Boveja et al. | |
| 2005/0187590 A1 | 8/2005 | Boveja et al. | |
| 2005/0283200 A1 | 12/2005 | Rezai et al. | |
| 2005/0283201 A1 | 12/2005 | Machado et al. | |
| 2005/0288760 A1 | 12/2005 | Machado et al. | |
| 2006/0079936 A1 | 4/2006 | Boveja | |

FOREIGN PATENT DOCUMENTS

| | | | |
|---|---|---|---|
| WO | 2004036377 A2 | 4/2004 | |
| WO | 2004112894 A1 | 12/2004 | |
| WO | 2005028026 A1 | 3/2005 | |
| WO | 2005065768 A1 | 7/2005 | |
| WO | 2003085546 | 4/2007 | |

OTHER PUBLICATIONS

Bachman, D.S, et al., "Effects of Vagal Volleys and Serotonin on Units of Cingulate Cortex in Monkeys," Brain Research, 130, (1977), pp. 253-269.

Clark, K.B., et al., "Enhanced Recognition Memory Following Vagus Nerve Stimulation In Human Subjects," Nature Neuroscience, vol. 2, No. 1, Jan. 1999, pp. 94-98.

Clark, K.B., et al., "Posttraining Electrical Stimulation Of Vagal Afferents With Concomitant Vagal Efferetn Inactivation Enhances Memory Storage Processes In The Rat," Neurobiology Of Learning And Memory 70, Article No. NL983863, (1998) pp. 364-373.

Devous, Sr., Michael D. et al., "Effects Of Vagus Nerve Stimulation On Regional Cerebral Blood Flow In Treatment-Resistant Depression," National Institute Of Mental Health 42nd Annual NCDEU Meeting, Poster Abstracts, Session II-19, 1 page. Found at: http://www.nimh.nih.gov/ncdeu/abstracts2002/ncdeu2019.cfm.

Dodrill, Carl B. et al., "Effects Of Vagal Nerve Stimulation On Cognition And Quality Of Life In Epilepsy," Epilepsy & Behavior, vol. 2, 2001, pp. 46-53.

Elger, Gerda et al., "Vagus Nerve Stimulation Is Associated With Mood Improvements In Epilepsy Patients," Epilepsy Research, No. 42, 2000, pp. 203-210.

Grundy, David, et al.., "Sensory Afferents From The Gastrointestinal Tract," Handbook of Physiology, John G. Forte et al, eds., American Physiology Society, Bethesda, Md., 1989, pp. 593-619.

Hallowitz, R.A., et al., "Effects of Vagal Volleys on Units of Intralaminar and Juxtalaminar Thalamic Nuclei in Monkeys," Brain Research, 130, (1977), pp. 271-286.

Henry, Thomas R., "Therapeutic Mechanisms Of Vagus Nerve Stimulation," Neurology, vol. 59, Suppl. 4, Sep. 2002, pp. S3-S14.

Koo, Betty, "EEG Changes With Vagus Nerve Stimulation," Journal Of Clinical Neurophysiology, vol. 18, No. 5, (Sep. 2001), pp. 434-441.

Leibowitz, Sarah F., "Eating Disorders and Obesity, A Comprehensive Handbook", Brownell and Fairburn, Ed., The Guilford Press, 1995, pp. 3-7.

Liebman, Kenneth M. et al., "Improvement In Cognitive Function After Vagal Nerve Stimulator Implantation," No. 3.080, Epilepsia, vol. 39, Suppl. 6, 1998, p. 93.

Ritter, R.C. et al., "Participation Of Vagal Sensory Neurons In Putative Satiety Signals From The Upper Gastrointestinal Tract," Neuroanatomy and Physiology of Abdominal Vagal Afferents, Sue Ritter et al, eds., CRC Press, 1992, pp. 222-244.

Rogers, R.C. et al., "Central Regulation Of Brainstem Gastric Vago-Vagal Control Circuits," Neuroanatomy and Physiology of Abdominal Vagal Afferents, Sue Ritter et al, eds., CRC Press, New York, NY, 1992, pp. 100-129.

Rush, A. John et al., "Continuing Benefit Of VNS Therapy Over 2 Years For Treatment-Resistant Depression," 43rd Annual New Clinical Drug Evaluation Unit Meeting, Boca Raton, Florida, May 27-30, 2003, 1 page.

Sackeim, Harold A. et al., "The Effects Of Vagus Nerve Stimulation On Cognitive Performance In Patients With Treatment-Resistant Depression," Neuropsychiatry, Neuropsychology, And Behavioral Neurology, vol. 14, No. 1, Jan. 2001, pp. 53-62.

Sheikh, Sohail et al., "Effects Of Vagus Nerve Stimulation Therapy On Brain Metabolism In Severe, Chronic Treatment-Resistant Depression: One-Year Outcome," 58th Annual Scientific Convention Of The Society Of Biological Psychiatry, San Francisco, California, May 15-17, 2003, 1 page.

Sjogren, Magnus et al., "Cognitive Effects Of VNS Therapy In Patients With Alzheimer's Deisease-Results Of A One-Year Clinical Trial," 58th Annual Scientific Convention Of The Society Of Biological Psychiatry, San Francisco, California, May 15-17, 2003, 1 page.

Terry, R.S., et al., "The Implantable Neurocybernetic Prosthesis System," Pacing and Clinical Electrophysiology, vol. 14, No. 1, (Jan. 1991), pp. 86-93.

Theodore, William H. et al., "Brain Stimulation For Epilepsy," The Lancet Neurology, vol. 3, Feb. 2004, pp. 111-118.

Woodbury, J.W., et al., "Vagal Stimulation Reduces the Severity of Maximal Electroshock Seizures in Intact Rats: Use of Cuff Electrode for Stimulating and Recording," PACE, vol. 14, (Jan. 1991), pp. 94-107.

Zabara, J., et al., "Inhibition of Experimental Seizures in Canines by Repetitive Vagal Stimulation," Epilepsia, 33(6), (1992), pp. 1005-1012.

* cited by examiner

SELECTIVE NEUROSTIMULATION FOR TREATING MOOD DISORDERS

BACKGROUND OF THE INVENTION

1. Field of the Invention

The present invention generally relates to methods and apparatus for stimulating certain areas of the brain to treat mood disorders by modulation of electrical activity of neural tissue in the selected area of the brain.

2. Description of Related Art

Recent developments in psychobiology and psychopharmacology have provided considerable evidence that major depressive disorder and bipolar depression are biological rather than psychological diseases. The conclusion that depression has a biological basis is also supported by numerous electrophysiological and endocrine studies. Deficiency of brain neurotransmitters has been associated with depression. In particular, abnormally low concentrations of the neurotransmitter serotonin and its metabolites and norepinephrine have been found in depressed patients. Several serotonin uptake inhibitors, which increase the amount of serotonin at the synapse have been shown to be effective antidepressants. Increased activity of the vagus nerve has been postulated to be associated with release of increased amounts of serotonin and norepinephrine in the brain.

U.S. Pat. No. 5,299,569 (Cyberonics, Inc.) discloses methods and devices for treating and controlling certain neuropsychiatric disorders by selective stimulation of the vagus nerve. A neurostimulator which is preferably, but not necessarily, implantable selectively applies the therapy to treat the specific neuropsychiatric disorder such as schizophrenia, depression, borderline personality disorder, or other related disorder. The therapy is delivered in a manner to stimulate or modulate the vagal activity of the patient in a predetermined manner to treat and relieve the symptoms of the disorder, although it may not be effective in alleviating the underlying root cause of the disorder. The neurostimulator is programmed by the attending physician to generate a pulsed electrical signal that provides the desired therapeutic modality for treatment.

U.S. Pat. No. 6,622,047 (Cyberonics, Inc.) discloses selective modulation of vagus nerve electrical activity using a neurostimulator device that may be implantable, or used external to the body with only a small portion of the circuitry implanted or with only the nerve electrode(s) and associated lead(s) implanted percutaneously in the body, to treat neuropsychiatric disorders including depression.

U.S. Pat. Nos. 6,418,344 and 6,609,030 (ElectroCore Techniques, LLC) describe methods for treating psychiatric diseases such as anxiety disorders and affective disorders by electrical or chemical neuromodulation of regions within the orbitofrontal cerebral cortex and the dorsomedial nucleus of the thalamus.

U.S. Patent Application Publication No. 2005/0027284 (Advanced Neuromodulation Systems, Inc.) describes electrical and/or chemical stimulation and transcranial magnetic stimulation applied to certain areas of the brain that exhibit altered activity in patients, relative to psychiatrically normal control subjects. Such stimulation is said to be produced by electrical stimulation, an excitatory neurotransmitter agonist (norepinephrine), an inhibitory neurotransmitter antagonist, and/or a medication (i.e., fluoxetine, trazodone) that increases the level of an excitatory neurotransmitter. An effective treatment site is said to be a subcallosal area including subgenual cingulate area, subcallosal gyrus area, ventral/medial prefrontal cortex area, ventral/medial white matter, Brodmann area 24, Brodmann area 25, and/or Brodmann area 10.

U.S. Pat. Nos. 6,263,237 and 6,128,537 (Medtronic, Inc.) describe certain techniques for treating an anxiety disorder by means of an implantable signal generator and electrode and/or an implantable pump and catheter, wherein the electrode and/or catheter are surgically implanted in the brain. The type of drugs administered into the brain depends on the specific location of delivery and the desired action on the neurons at that location. Electrical stimulation of amygdala, dorsal raphe nucleus, septum, frontal cortex, anterior nucleus of thalamus, mammillary body, parenchyma, anterior limb of the internal capsule, head of the caudate nucleus, cingulum fibers, cingulate gyrus, dorsal medial nucleus of thalamus and locus ceruleus, are described.

U.S. Pat. No. 6,176,242 (Medtronic, Inc.) similarly describes techniques for treating depression or manic depression by deep brain stimulation at certain sites in the brain.

U.S. Pat. No. 6,708,064 (Rezai) describes a method for treating neurological conditions by proper placement of a probe and sensing certain areas of the brain, especially the intralaminar nuclei, to affect psychiatric disorders.

Alternative ways to treat patients suffering from severe or life threatening depression or other mood disorder that is not sufficiently responsive to conventional therapies are needed.

SUMMARY OF THE INVENTION

The inventors propose that selective deep brain stimulation (DBS) together with cranial nerve stimulation is beneficial for treating mood and anxiety disorders when certain areas or regions of the brain are appropriately stimulated. Combined cranial nerve stimulation and DBS is expected to offer advantages over conventional therapies. The preferred areas of the brain selected for treatment are those which are associated with symptoms of the mood disorder to be treated. Bimodal treatment (e.g., electrical and chemical) is expected to be especially beneficial. Mood disorders for which treatment is contemplated include, but are not limited to, depression, major depressive disorder, bipolar disorder, dysthymic disorder, anxiety disorders. Anxiety disorders include, but are not limited to, obsessive compulsive disorder (OCD), post-traumatic stress syndrome (PTSD), panic disorder, generalized anxiety, simple phobia and social phobia. For ease of reference, the use of the term "mood disorder" herein also includes the above-named disorders.

In accordance with certain embodiments of the present invention a method of treating an individual suffering from a mood disorder is provided in which the method includes: coupling a first stimulator to a predetermined area of the individual's brain comprising a volume of neural tissue associated with a symptom of the mood disorder, the predetermined area chosen from the group consisting of insula, subcallosal area, cingulate, thalamus, hypothalamus, prefrontal cerebral cortex, brain stem, cerebellum, and white matter tracts leading to an aforementioned area; and applying a first therapeutic stimulation signal to the first stimulator such that the neuronal activity of the neural tissue is modified, wherein such modification of neuronal activity alleviates a symptom of the mood disorder or deters onset of the symptom. In certain embodiments, the first stimulator comprises an electrode and the first therapeutic stimulation signal comprises an electrical signal, and the method includes coupling the electrode to the area of the individual's brain; and applying the first predetermined electrical signal to the electrode such that the neuronal activity of the neural tissue is modified, wherein such modification of neuronal activity alleviates a symptom of the mood disorder or deters onset of the symptom. In certain embodiments, the first stimulator comprises a chemical stimulation device comprising a catheter having a proximal end coupled to a pump and a discharge portion for infusing a chemical agent, as described above, and the first therapeutic stimulation signal comprises a predetermined pumping signal, and the method further includes placing the discharge portion of the catheter at the selected area of the individual's brain; and then applying the first predetermined pumping signal to the chemical stimulation device such that the chemical agent is released from the discharge portion and contacts the neural tissue, whereby the neuronal activity of the neural tissue is modified and such modification of neuronal activity alleviates a symptom of the mood disorder or deters onset of the symptom.

In certain embodiments of the present invention, application of an above-described first therapeutic stimulation signal alleviates a symptom of the disorder or deters onset of the symptom in the individual. In certain embodiments, the predetermined or selected brain area is an insula area such as the left anterior insula, the right anterior insula, the left posterior insula or the right posterior insula, or a white matter tract leading to one of those areas.

Similarly, in certain above-described methods that employ a second therapeutic stimulation signal, the second signal also comprises an acute stimulation component and a chronic stimulation component. The acute stimulation component may include a higher intensity level of stimulation and shorter duration than the chronic stimulation component.

Further provided in accordance with certain embodiments of the present invention is a method of modulating neuronal activity in a subcallosal area of the brain of an individual known to, or suspected of having a severe mood disorder and/or anxiety disorder. The method includes surgically implanting a stimulation device in communication with a subcallosal area, or a white matter tract leading to a subcallosal area; and operating the device to stimulate the selected subcallosal area, and thereby modulating neuronal activity in the area in the individual. In certain embodiments, neuronal modulation of a subcallosal area enhances the mood of the individual. In certain embodiments, the surgical implantation of the stimulation device comprises obtaining a stimulation device comprising an electrical stimulation lead having a proximal end and a stimulation portion; and obtaining a signal generator; surgically implanting the electrical stimulation lead having a proximal end and a stimulation portion such that, after implantation the stimulation portion is in communication with a subcallosal area; and coupling the proximal end of the lead to a signal generator. Operating the device comprises generating an electrical signal with the signal generator and applying the electrical signal to the stimulation portion, whereby the signal electrically stimulates a subcallosal area and thereby treats the mood and/or anxiety disorder.

In accordance with certain embodiments of the present invention a method of treating a patient suffering from a mood disorder is provided, the method comprising: coupling a first electrode to a cranial nerve of the patient; coupling a second electrode to a selected brain area of the patient, wherein neuronal activity in the predetermined area is correlatable to at least one symptom of the mood disorder. Suitable target areas include, but are not limited to, the following areas of the brain: insula, subcallosal area, cingulate, thalamus, prefrontal cerebral cortex, brain stem, cerebellum, and white matter tracts leading to an aforementioned area. A predetermined electrical signal is applied to the cranial nerve using the first electrode; and electrical activity is sensed in the selected brain area using the second electrode, to detect modulation of neuronal activity in the a selected brain area resulting from the application of the therapeutic electrical signal. In certain embodiments, the method further includes correlating the detected modulation of neuronal activity with alleviation of a symptom of the mood disorder in the patient. The cranial nerve is preferably one or more of the vagus, trigeminal, hypoglossal or accessory nerves. In some embodiments stimulation is bilateral, with stimulation of both left and right vagus nerves, in synchrony or asynchronously, in order to selectively inhibit, excite, or block selective areas of the brain to provide a therapeutic effect. In certain embodiments the method includes adjusting a stimulation device to provide timing of bursts of electrical bilateral stimulation to attenuate the neural activity in selective areas of the brain.

In some embodiments, a method of treatment includes providing a controller comprising a signal generator and processor in communication with a first electrode and a second electrode; directly coupling the first electrode to a cranial nerve of the in patient; directly coupling the second electrode to an area of the patient's brain selected from the group consisting of insula, subcallosal area, cingulate, thalamus, prefrontal cerebral cortex, brain stem, cerebellum, and white matter tracts leading from an aforementioned area; applying the therapeutic electrical signal to the first electrode; sensing electrical activity in the selected area of the brain with the second electrode; comparing the sensed electrical activity to a predetermined reference state, yielding comparison results; and determining from the comparison results whether the application of the predetermined electrical signal to the first electrode causes a modulation of neuronal activity in the selected brain area, wherein the modulation of neuronal activity corresponds to a therapeutic benefit (e.g., alleviation of a symptom of the mood disorder). In some embodiments, the method further includes adjusting the predetermined signal according to the comparison results, to alter the modulation of neuronal activity in the selected brain area and enhance alleviation of a symptom of the mood disorder.

Also provided in accordance with certain embodiments of the present invention is a method of treating a patient suffering from a mood disorder in which the method includes directly coupling a first stimulator to a cranial nerve (e.g., a vagus nerve) of the patient; directly coupling a second stimulator to a brain area of the patient selected from the group consisting of insula, subcallosal area, cingulate, thalamus, hypothalamus, prefrontal cerebral cortex, brain stem, cerebellum, and white matter tracts leading to an aforementioned area; applying a first therapeutic signal to the cranial nerve using the first stimulator; and applying a second therapeutic signal to the brain area using the second stimulator, wherein the application of the first and second signals causes modulation of electrical activity in at least one the brain area correlatable to alleviation of a symptom of the mood disorder in the patient or deters onset of the symptom. In some embodiments the first stimulator is a first electrode and the second stimulator is a second electrode, and the method further comprises providing at least one programmable electrical pulse generator coupled to the first and second electrodes; programming at least one electrical pulse generator to define each of the first and second electrical signals by a plurality of parameters comprising a current magnitude, a pulse frequency, and a pulse width, wherein the parameters are selected to alleviate a symptom of the mood disorder.

In accordance with certain embodiments of the present invention, the first therapeutic signal of an above-described method comprises at least an acute stimulation component and a chronic stimulation component, wherein each of the components comprises a set of electrical parameters (current, pulse width, frequency), on/off times and duration of stimulation. In certain embodiments, the acute stimulation component comprises a higher intensity level of stimulation and shorter duration than the chronic stimulation component. Higher intensity stimulation comprises higher electrical parameters, on/off times and duration. In some embodiments, the acute stimulation component comprises a duration of about one to six months.

In accordance with certain embodiments of the present invention, the second therapeutic stimulation signal of an above-described method also comprises at least an acute stimulation component and a chronic stimulation component, each component comprising a set of electrical parameters, on/off times and duration. In some embodiments, the acute stimulation component of the second signal includes a higher intensity level of stimulation and shorter duration than the chronic stimulation component of the second signal. In some embodiments, the acute stimulation component of the second stimulation signal comprises a duration of one to six months.

In accordance with certain embodiments of the present invention, the area of the brain selected for stimulation in an above-described method comprises at least a portion of the insula, or a white matter tract leading to the insula. In some embodiments, the selected area comprises a portion of the insula chosen from the group consisting of the left anterior, right anterior, left posterior and right posterior insula. In some embodiments, the selected area comprises a subcallosal area or a white matter tract leading to a subcallosal area. In some embodiments, the selected area of the brain comprises at least a portion of a Brodmann area within the cingulate chosen from the group consisting of Brodmann area 24 and Brodmann area 25, or a white matter tract leading to the Brodmann area. In certain embodiments, the selected area of the brain includes at least a portion of a Brodmann area within the prefrontal cortex, or a white matter tract leading to the Brodmann area. For instance, the selected area may comprise the orbitofrontal cortex and/or at least a portion of any of Brodmann areas 8-11. In still other embodiments, the selected area of the brain comprises the thalamus, brainstem, cerebellum, or midbrain, or at least one nucleus therein, or a white matter tract leading to the nucleus. In some embodiments the selected area comprises a pontine or medullary nucleus, such as the locus coeruleus, NTS, dorsal raphe or PBN.

In certain embodiments, the treatment method includes application of the second therapeutic signal electrically such that stimulation of the subgenual cingulate area, or a white matter tract leading to the subgenual cingulate results in improvement of the mood disorder. In some embodiments, applying the second therapeutic signal comprises applying the second stimulation signal to a site in the subgenual cingulate to cause a modulation of neuronal activity in a Brodmann area of the brain, preferably one or more of Brodmann area 25, Brodmann area 24, Brodmann area 10 and Brodmann area 9. In certain embodiments, the second stimulator comprises a chemical stimulation device comprising a catheter having a proximal end in fluid communication with a pump and a discharge portion for infusing a chemical at the selected site, and the second therapeutic signal comprises a predetermined pumping signal, the method comprising: coupling the discharge portion to a selected area of the individual's brain; and applying the predetermined pumping signal to the chemical stimulation device such that the chemical is released from the discharge portion and contacts the neural tissue, whereby the neuronal activity of the neural tissue is modified and such modification of neuronal activity alleviates a symptom of the mood disorder or deters onset of one or more symptoms of the disorder. The chemical agent is an inhibitory neurotransmitter agonist or antagonist, an excitatory neurotransmitter agonist or antagonist, an agent that increases the level of an inhibitory neurotransmitter, an agent that decreases the level of an excitatory neurotransmitter, or a local anesthetic agent, for example.

Still further provided in accordance with certain embodiments of the present invention is an adaptive brain stimulation process for treating a patient suffering from a mood disorder. The process comprises (a) providing a system comprising at least one sensor for coupling with a patient to sense a present state of at least a first brain region or set of brain regions; at least one stimulating circuit for coupling with at least the first brain region or set of brain regions by at least one stimulation electrode, to carry out stimulation according to a first set of stimulation parameters; a comparator coupled with the at least one sensor, the comparator adapted for receiving data related to the present state and comparing the present state data with reference state data, such that the comparing results in a positive outcome or a negative outcome; and at least one control circuit coupled with the at least one stimulating circuit adapted for being adjusted according to the outcome of the comparing of the present and reference states, to control the stimulation parameters; (b) coupling the at least one sensor with the a status indicator site on a patient; (c) stimulating a first brain region or a first set of brain regions of the patient according to a first set of stimulation parameters; (d) sensing a present state of the patient to provide sensed data, e.g., sensing neuronal activity of a peripheral cranial nerve); (e) comparing the sensed data with reference state data to derive comparison results; (f) determining from the comparison results whether a change in the stimulation parameters is necessary (e.g., no change is necessary when stimulation according to a changed set of stimulation parameters ameliorates a symptom of the mood disorder); (g) if the change is necessary, determining what changes are to be made in the stimulation parameters; (h) changing the first stimulation parameters as determined in step (f); and (i) repeating steps (c)-(h) until no further change is determined to be necessary in step (g). In some embodiments, the process also includes stimulating a second brain region or a second set of brain regions of the patient if the comparison results indicate that a response signal causes a therapeutic benefit. In some embodiments, the step of stimulating a second brain region or a second set of brain regions causes a beneficial therapeutic effect. These and other embodiments, features and advantages will be apparent from the following detailed description and drawings.

BRIEF DESCRIPTION OF THE DRAWINGS

FIG. 4A is a sagittal sectional view of the brain depicting a representative insula stimulation site of the brain, and FIG. 4B is a coronal sectional view of the brain depicting representative prefrontal cortex, cingulate, thalamus and brain stem treatment sites.

DETAILED DESCRIPTION OF THE PREFERRED EMBODIMENTS

Definitions

Figure 1:
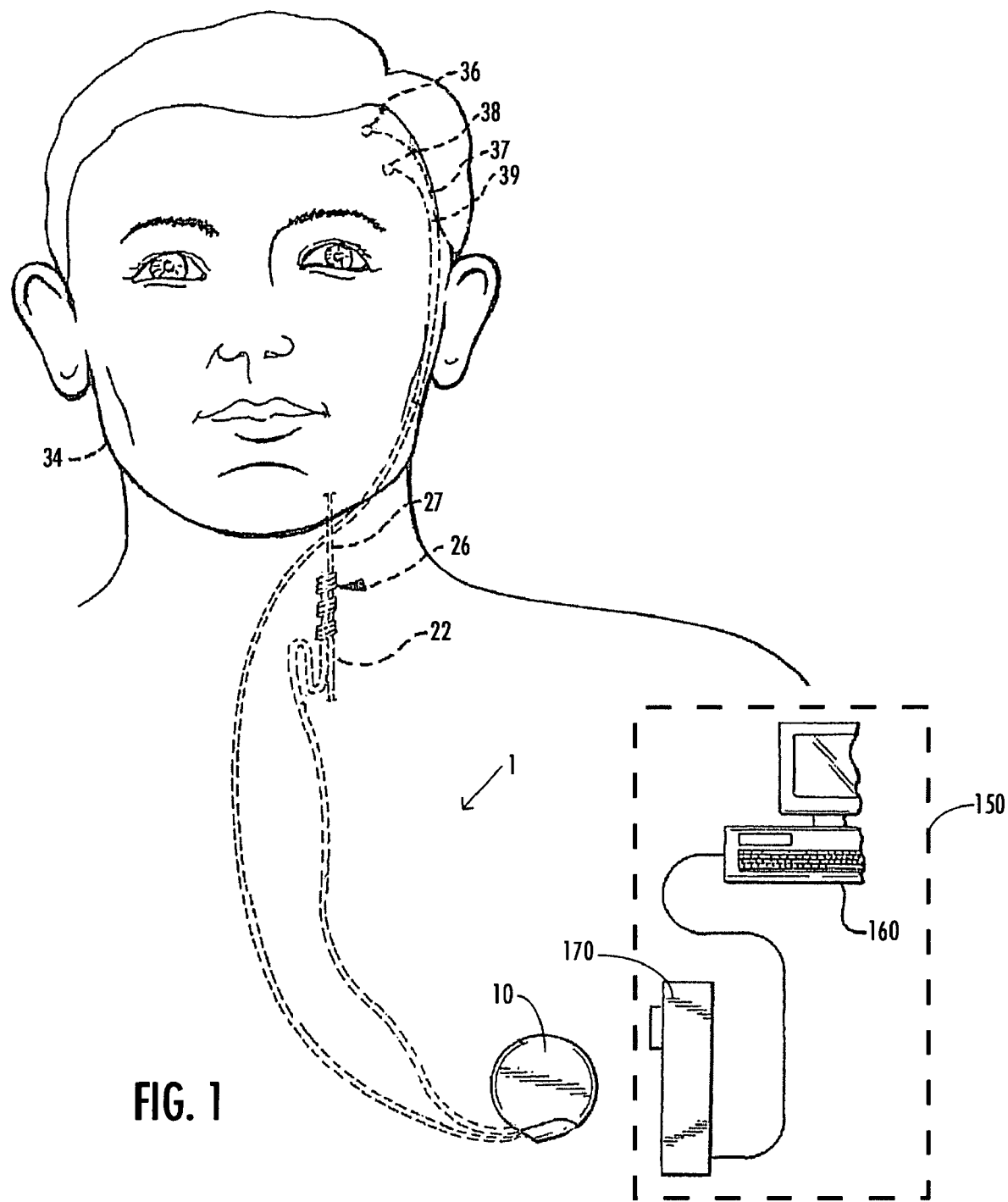
FIG. 1 is a simplified illustration of an electrode and neurostimulator placement configuration for treating an mood disorder in accordance with an embodiment of the present invention.

The term "mood disorder" refers to depression, major depressive disorder, bipolar disorder, dysthymic disorder, anxiety disorders. Anxiety disorders include, but are not limited to, obsessive compulsive disorder (OCD), post-traumatic stress syndrome (PTSD), panic disorder, generalized anxiety, simple phobia and social phobia. Use of the term "mood disorder" herein also refers to one or more of the above-named disorders.

As used herein, the terms "stimulating" and "stimulator" generally refer to delivery of a signal, stimulus, or impulse to neural tissue for affecting neuronal activity of a neural tissue (e.g., a volume of neural tissue in the brain or a nerve). The effect of such stimulation on neuronal activity is termed "modulation"; however, for simplicity, the terms "stimulating" and "modulating," and variants thereof, are sometimes used interchangeably herein. The effect of delivery of the signal to the neural tissue may be excitatory or inhibitory and may potentiate acute and/or long-term changes in neuronal activity. For example, the effect of "stimulating" or "modulating" a neural tissue may comprise one or more of the following effects: (a) changes in neural tissue to initiate an action potential (bi-directional or uni-directional), (b) inhibition of conduction of action potentials (endogenous or externally stimulated) or blocking the conduction of action potentials (hyperpolarizing or collision blocking), (c) affecting changes in neurotransmitter/neuromodulator release or uptake, receptors, gated ion channels or synapses which can be excitatory, inhibitory or of a blocking nature, and (d) changes in neuro-plasticity or neurogenesis of brain tissue.

"Deep brain stimulation" (DBS) refers to direct or indirect application of a stimulus to an area within the brain. Such stimulation may be electrical, chemical (e.g., drug or pharmaceutical), or magnetic and may be applied directly or indirectly to the neural tissue of the brain. Similarly, deep brain sensing refers to the detection of an electrical or chemical signal from within the brain.

For ease of reference, "cranial nerve stimulation" is sometimes referred to herein simply as "VNS".

The terms "couple," "couples," "coupled," and "coupling" refer to either indirect or direct electrical connection.

"Predetermined electrical signal" or "therapeutic electrical signal" refers to an electrical pulse, or pattern of electrical pulses, having defined parameters such as pulse current, pulse width, frequency, on-time and off-time.

"Chemical stimulation" and "chemical agent" refer to either chemical, drug or pharmaceutical agents capable of stimulating neuronal activity in a nerve or in neural tissue exposed to such agent. Examples of such agents are inhibitory neurotransmitter agonists, excitatory neurotransmitter antagonists, agents that increases the level of an inhibitory neurotransmitter, agents that decrease the level of an excitatory neurotransmitter, and local anesthetic agents.

Description

The inventors propose that neural circuitry of the brain involved with symptoms of depression and other mood disorders comprise neurons in certain areas of the brain that have not been previously correlated with causation or alleviation of mood disorders. Those areas are believed to comprise nodes in the neural circuitry that relate to the manifestation of mood disorders, and may be modulated to affect the presence, absence or degree of depression, anxiety, or other mood disorder in an individual. The inventors propose that the combination of cranial nerve stimulation and brain stimulation is useful for optimizing brain stimulation signal parameters, and that the therapeutic combination of VNS and DBS provides an effective treatment strategy for patients suffering from serious mood disorders. Target sites of particular interest for brain stimulation and/or sensing include, but are not limited to, insula, subcallosal area, cingulate, thalamus, prefrontal cerebral cortex, brain stem, cerebellum, and white matter tracts leading to or from an aforementioned area or to a Brodmann area or nucleus therein. Preferred stimulation sites for VNS are one or more of the vagal, hypoglossal, trigeminal and accessory nerves. It is also proposed that sensing of neuronal activity may be beneficially employed in conjunction with modulation of one or more of those areas of the brain to adapt or modify stimulation parameters of a neurostimulation system and to optimize or enhance a therapeutic treatment regimen for treating an individual patient's mood disorder.

Deep Brain Stimulation (DBS) System for Treatment of Mood Disorders

Referring to FIG. 1, a neurostimulator system 1 is shown as configured for treating depression or other mood disorder in a patient 34 (shown in phantom line) by modulating the electrical activity of selected areas of the brain that are associated with symptoms of the disorder. System 1 generally includes at least one implantable stimulator device (stimulator) 36, preferably an electrode in communication with a microprocessor-based control device (controller) 10.

Figure 2:
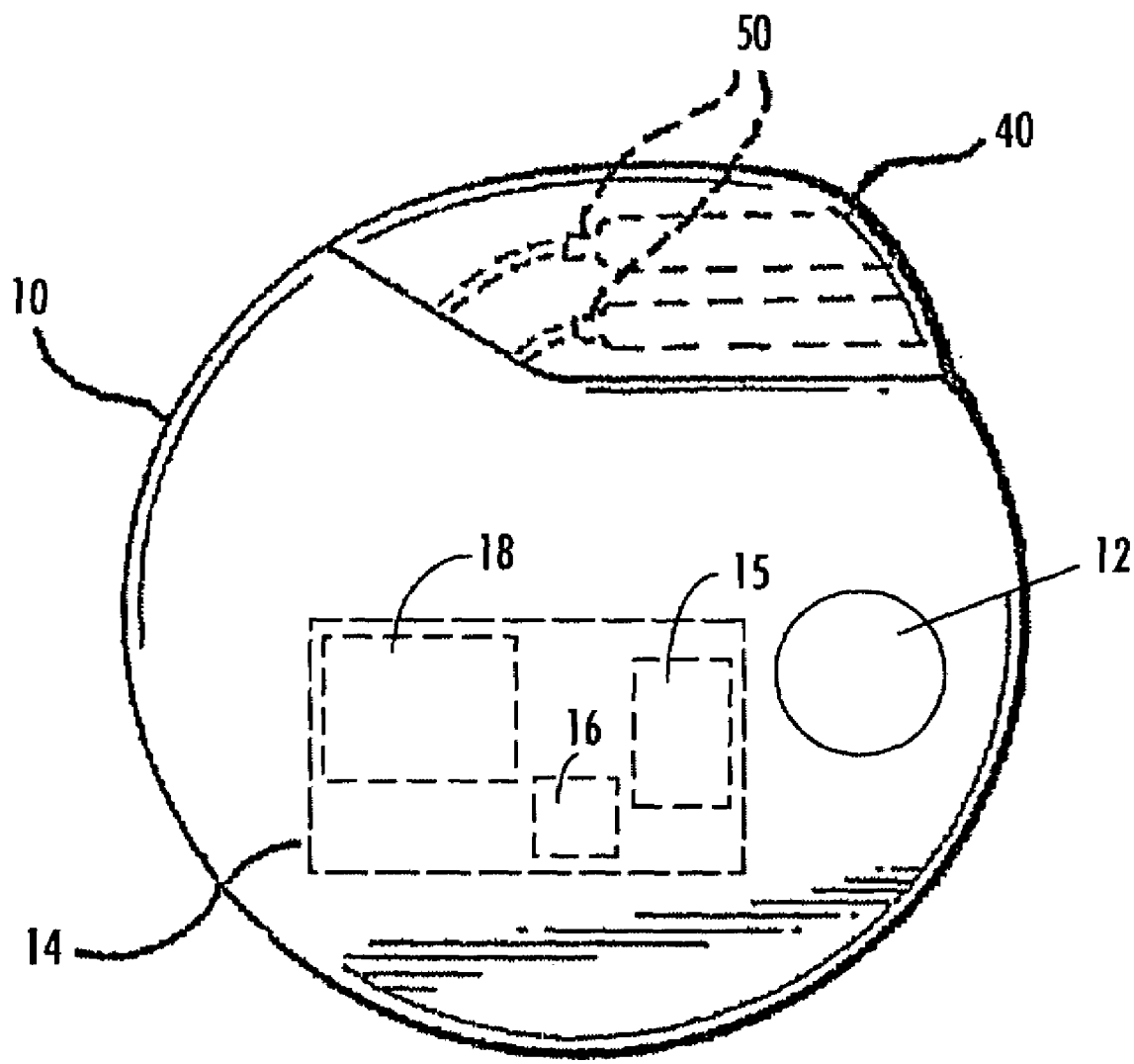
FIG. 2 is a fragmentary illustration of a controller containing a battery and programmable electronics package (shown as a block diagram), for use in treating an mood disorder in accordance with an embodiment of the present invention.

Stimulator. For ease of reference, the stimulator or stimulus applicator is sometimes referred to herein as simply "the electrode." It should be understood, however, that stimulation of a nerve or neural tissue can be electrically, chemically or magnetically mediated, or a combination of any or all of those modes. An electrode is designed for placing in direct contact with a volume of neural brain tissue to be stimulated and/or sensed, as may be required. Alternatively, at least one electrode is selected which is suitable for placement in proximity to the target neural tissue. For electrical stimulation mode, the controller 10 is coupled to each electrode 36 by transcranial lead(s) 37, and is designed for applying an electrical signal to the selected area using the electrical signal generator unit 15 of controller 10 (FIG. 2). Lead(s) 37, 39 attach to the controller 10 at connectors 50 of header 40. Electrode/lead assemblies of this type are commercially available from known suppliers. Alternatively, lead(s) 37 is/are omitted and at least one implanted electrode comprises an induction receiver and controller 10 is configured to remotely modulate the target neural tissue through telemetry via an external transmitter. A suitable electrode of this type is commercially available from known suppliers.

Sensor. The system may include at least one implantable sensing electrode (sensor) 38. The sensor is designed to measure endogenous neural activity or activity induced by modulation through actions of the controller 10 and is in communication with the control device 10 via lead(s) 39. Accordingly, the system may be adapted for applying the stimulation signal in response to a preselected triggering event, from sensed physiological activity, from an external actuator, from brain imaging data, or from physician or patient input, as discussed in more detail below. Suitable sensing electrodes and other sensing devices capable of sensing physiological parameters are commercially available from known sources.

Controller. Certain parameters of the stimuli generated by the controller are programmable. System 1 comprises an internal or external system capable of measuring, sensing, recording, monitoring the physiological activity, physiological event, physiological threshold, body or brain state. Additionally, the system may be designed to vary the treatment parameters, based on adaptive learning whereby the device senses activity or physiologic changes after stimulation and automatically adjusts the controller to attempt to deliver optimized therapy. In that case, the controller can also sense the result of adverse stimulation and adjust the stimulation to prevent an adverse patient response.

As shown in FIG. 1, an external programming system 150 is employed in a conventional manner for implantable electrical medical devices. External programming system 150 is preferably capable of wireless (e.g., radio frequency) communication with the controller 10, and comprises a computer 160 and a wand 170 having an RF transmitter and receiver. Computer 160 may comprise a handheld computer operable by a healthcare provider. Wand 170 is capable of communicating with a receiver and transmitter in controller 10, and may be used to receive data from or transmit data to the controller 10.

Alternatively, the implantable control device 10 comprises a programmable electronics package 14 containing a signal generator 15, a monitoring unit (monitor) 16 for transmitting control signals to/from the implanted electrode(s) and sensor(s), as appropriate, and a processing unit (processor) 18 for recording, measuring, sensing or monitoring physiologic data and comparing it to stored values, baseline values, reference or expected values and performing calculations on best treatment parameters (as schematically illustrated in FIG. 2). A power source 12 is also contained in controller 10. The programmable processor is configured to adjust and transmit stimulus parameters to the stimulator assembly in order to treat the disorder. The monitoring data can be stored digitally for future processing or diagnosis. A generally suitable form of implantable controller/pulse generator for use in the system and method of the present invention is disclosed, for example, in U.S. Pat. No. 5,154,172, assigned to the same assignee as the instant application (the device also referred to as a NeuroCybernetic Prosthesis or NCP device (NCP is a trademark of Cyberonics, Inc. of Houston, Tex., U.S.A.)

Figure 3:
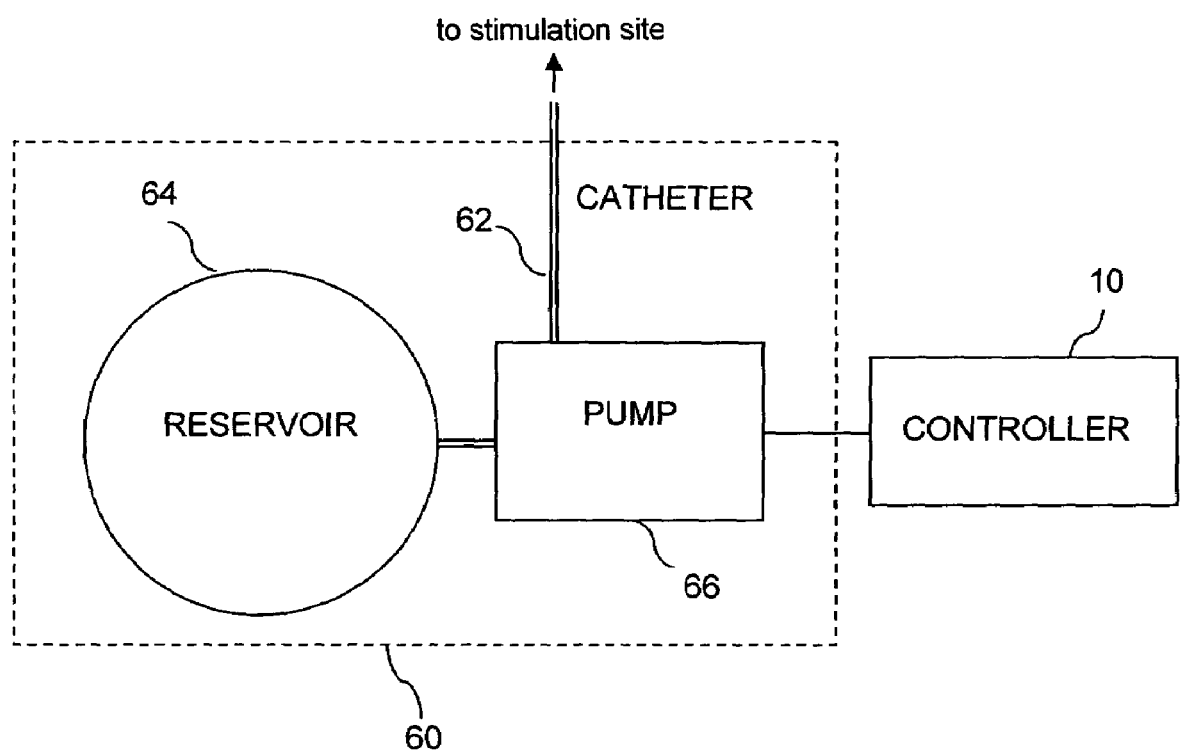
FIG. 3 is a schematic block diagram showing a chemical stimulation assembly according to an embodiment of the present invention.

Electrical, chemical, magnetic stimulation. Although the use of one or more electrodes as the stimulus application device (stimulator) for delivering electrical stimulation to the target neural tissue is preferred, it is also contemplated that the neurostimulator system could instead, or additionally, include a chemical or pharmaceutical applicator for applying a therapeutic stimulus to the target neural tissue effective to modulate the activity of the neural tissue to ameliorate the mood disorder. The chemical stimulus application device 60 may comprise a chemical-filled reservoir 64 in fluid communication with a catheter 62 and pump 66 that is either implantable or has both implantable (catheter) and external (pump) components, or another suitable chemical delivery device could be included in the system (FIG. 3). The pump is coupled to controller 10. Examples of the types of chemicals or drugs that may be beneficially employed are inhibitory neurotransmitter agonists or antagonists, excitatory neurotransmitter agonists or antagonists, chemicals that increases the level of an inhibitory neurotransmitter, chemicals that decrease the level of an excitatory neurotransmitter, and local anesthetics. Control signals may be transmitted to or from either an electrode on the nerve, electrode or sensor in the brain, from a chemical delivery device and/or sensor, or from an internal or external monitoring unit via telemetry and/or through signals transmitted through conductive leads, as provided in the programmable circuitry.

In another configuration of the neurostimulation system, the stimulator is omitted and the system is designed for non-invasively applying a magnetic stimulus to a selected nerve or neural tissue from an external source via a transcranial magnetic stimulator (not shown), as are known in this field. Accordingly, it should be appreciated that neural tissue modulation can be electrically, magnetically or chemically/pharmaceutically mediated.

Still another configuration of the neurostimulation system substitutes an electrode designed for dural or subdural placement adjacent an area of the brain such as the orbitofrontal cortex area, instead of using an electrode for deep brain implantation. Dural or subdural electrodes may be designed for applying electrical stimulation or for sensing electrical activity, or both.

In still another configuration of the system, also shown in FIG. 1, the neurostimulation system includes at least one stimulator and/or sensor 26 for coupling directly or indirectly to at least one cranial nerve 27, preferably the trigeminal, hypoglossal, vagus or accessory nerve. Sensor 26 is coupled to controlled 10 by lead 22. Alternatively, electrodes suitable for placement on, or proximal to, the left and/or right vagus nerve(s) in a near-diaphragmatic location (e.g., supra-diaphragmatic or sub-diaphragmatic) may be included in the system. These may be stimulating and/or sensing electrodes.

An adaptive brain stimulation system comprises one or more biological sensors coupled to a patient for sensing a present state of at least a first brain region or a first set of brain regions. At least one stimulating circuit is coupled with at least the first brain region or first set of brain regions of the patient by at least one electrode to carry out stimulation according to a set of stimulation parameters. The system also comprises a comparator coupled with the sensors to receive data related to the present state and compare the present set data with reference state data, wherein the comparison leads to a positive outcome or a negative outcome. The at least one control circuit coupled with at least one stimulating circuit is able to be adjusted according to the outcome of comparing the present and reference states, to control the set of stimulation parameters.

Programmable control. The control device is designed so that control signals are transmitted from an internal or external monitoring unit to the electrode(s) and/or sensor(s). The system is capable of delivering stimulation that can be intermittent, periodic, random, paired-pulses, coded or patterned. For example, electrical stimulation frequency can be 0.1 to 2500 Hz, pulse width 1-2000 micro seconds, current amplitude 0.1 mA to 10 mA. Stimulation can occur through either the cathode (−) electrode or positive (+) electrode.

The neurostimulation system 1 is preferably capable of delivering to the target neural tissue a stimulatory electrical signal that can be intermittent, periodic, random, paired-pulses, coded or patterned. Stimulation frequency can be 0.1 to 2500 Hz, pulse width 1-2000 micro seconds, current amplitude 0.1 mA to 10 mA. Stimulation can occur through either the cathode (−) electrode or positive (+) electrode.

Manual activation/deactivation. The system design may be varied to provide a manual activation or deactivation switch in association with controller 10. Similar devices for manual and automatic activation of implantable medical devices are known, such as are disclosed in U.S. Pat. No. 5,304,206 (Cyberonics, Inc.). For example, manual activation or deactivation of the signal generator is achieved using a device such as an accelerometer or a piezoelectric element mounted to the inner surface of the controller housing so as to detect light taps by the patient on the controller implant site in the patient's body. This design provides for the patient to have limited but convenient control over the device operation, to the extent that the physician determines is appropriate.

Method of Treating a Mood Disorder

VNS and/or DBS. At least one stimulator (e.g., electrode, catheter) is implanted in contact with, or in proximity to, one of the cranial nerves and/or a volume of neural tissue. The cranial nerve being preferably the trigeminal, hypoglossal, vagus and/or accessory nerve. Stimulators may be coupled to one or more cranial nerves, contacting each selected nerve at any point along its length or one of the nerve branches. For instance, stimulators may be placed bilaterally, e.g. both left and right vagus nerves. Similarly, at least one sensor (e.g., sensing electrode) is implanted in contact with, or in proximity to, one of the cranial nerves and/or a volume of neural tissue. Depending upon the desired mode of treatment to be administered, the procedure may include implanting a selected type of stimulator/sensor device (e.g., stimulating and/or sensing electrode and/or plurality of electrodes, chemical catheter, sensor) in contact with neural tissue in the brain. Alternatively, or additionally, the surgical procedure may include implanting a device (stimulating and/or sensing electrode and/or plurality of electrodes, and/or chemical catheter, sensor) in contact with tissue in the patient's viscera, organs or peripheral nervous system.

FIG. 1 illustrates a preferred location of implanted controller 10 in the patient's chest in a cavity formed by the implanting surgeon just below the skin, much as a pacemaker pulse generator would be implanted. A representative treatment regimen to assist a patient in overcoming a serious mood disorder (e.g., persistent or repeated episodes of severe depression) generally includes obtaining an above-described neurostimulation system that is configured and programmed or programmable to modulate neuronal activity of a predetermined area of neural tissue.

Figure 4A:
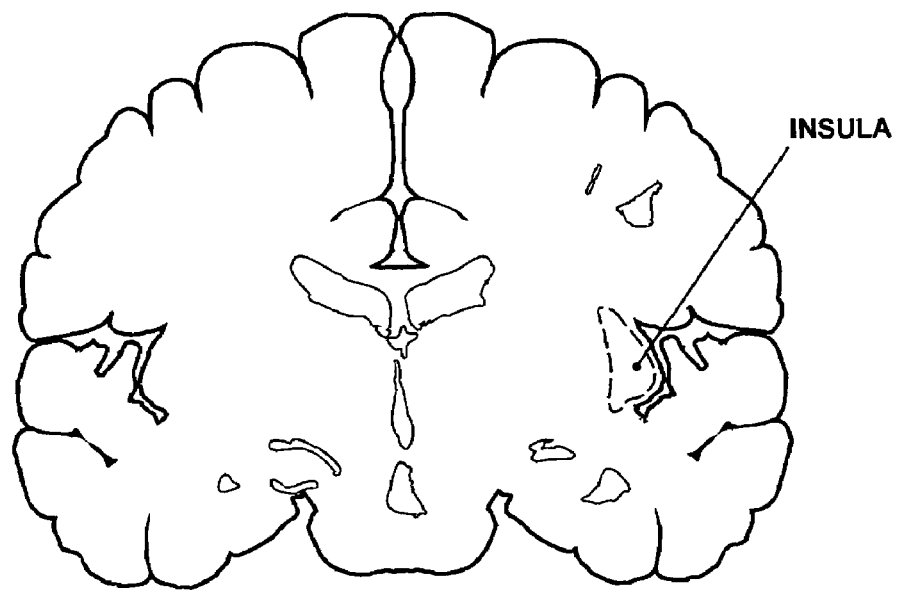
FIGS. 4A-B are simplified illustrations of stimulator placement sites in selected areas of the brain of a patient for treatment of an mood disorder, in accordance with certain embodiments of the present invention.
Figure 4B:
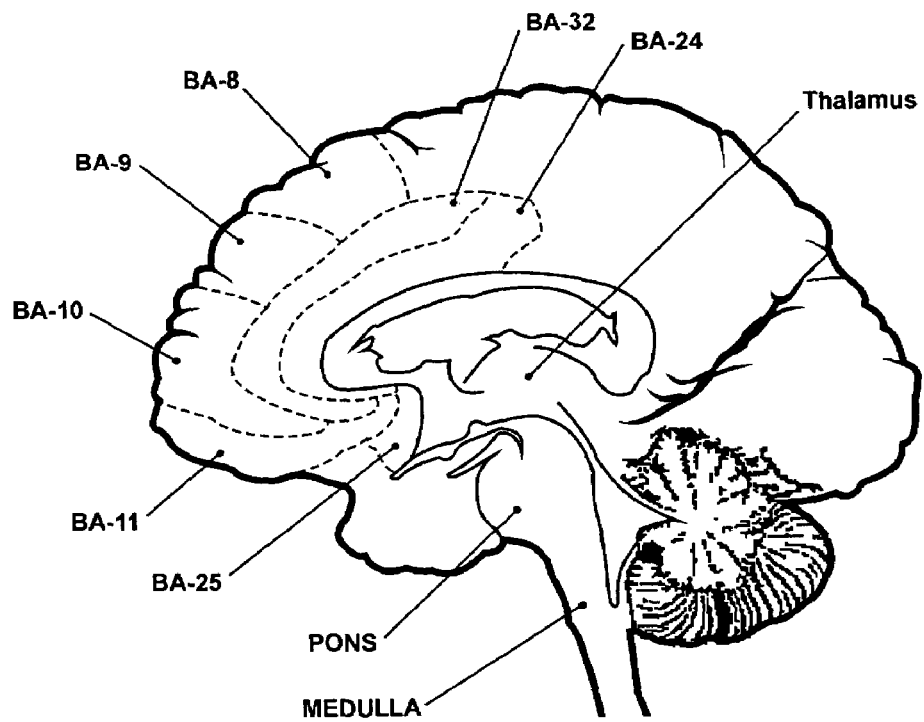

At least one stimulator 36 (e.g., electrode) is surgically implanted in the brain of a patient in need of treatment for a serious mood disorder. Employing appropriate surgical techniques as are known in the art, a small opening is made in the skull and the stimulator is placed in, or proximal to, an area of the brain that comprises a "node" in the neural circuitry which is correlated with symptoms of the patient's mood disorder. For example, the target area may be associated with feelings of sadness or hopelessness. A representative stimulator implantation location is a site in the insula, as indicated in FIG. 4A. The left and right anterior and posterior insula and the claustrum are suitable modulation sites. Other preferred stimulator implantation sites are a subcallosal area, cingulate, thalamus, prefrontal cortex, cerebellum, midbrain and brainstem, and the nuclei or Brodmann areas within those regions, and white matter tracts leading to or from any of those areas (FIG. 4B). Brodmann areas 24, 25 and 32, or a portion of any of those, are preferred stimulation sites. The parafascicular nucleus is another preferred site. Brodmann areas 8, 9, 10 and 11, and the orbitofrontal cortex, or a portion of one or more of those areas are also preferred stimulation sites. The pontine and medullary regions are additionally preferred implantation sites. While the figures and description focus on one hemisphere of the brain, it should be understood that stimulation and/or sensing of like structures on either or both sides of the brain is also contemplated. Stimulation and/or sensing may be applied to sites in one or both hemispheres and may be carried out in at the same time or at different times, and may comprise the same or different stimuli.

Areas of the brain that are of interest as stimulation and/or sensing sites include, but are not limited to, centromedian fascicular complex, hippocampus, ventral medial Vim thalamic nucleus, parafascicular complex, other portion of the thalamus, entirety of the thalamus, subthalamic nucleus (STN), caudate, putamen, other basal ganglia components, cingulate gyros, other subcortical nuclei, nucleus locus ceruleus, pedunculopontine nuclei of the reticular formation, red nucleus, substantia nigra, other brainstem structure, cerebellum, internal capsule, external capsule, corticospinal tract, pyramidal tract, ansa lenticularis, limbic circuit of Papez, the fronto-basal ganglionic-thalamocortical system, white matter tracts, motor cortex, premotor cortex, somatosensory cortex, other sensory cortical regions, Broca's area, Wernickie's area, ventricular region, paraventricular region, other central nervous system structure, other peripheral nervous system structure. The cortex, limbic system and reticular system, pre-frontal cortex, orbitofrontal cortex, anterior limb of the internal capsule, nucleus accumbens, ventral striatum, the ventral pallidum anterior nucleus of the thalamus, dorsomedial nucleus of the thalamus, intralaminar thalamic nuclei, the cingulate cortex, amygdala, hippocampus, mamillary bodies, the lateral hypothalamus, the locus ceruleus, the dorsal raphe nucleus, parabrachial nucleus (PBN), nucleus of the solitary tract (NTS), the caudal ventrolateral medulla (CVL), and rostral ventrolateral medulla (RVL), paraventricular nucleus of the hypothalamus, parafascicular nucleus, the bed nucleus of the stria terminalis, the prefrontal cortex, the supraoptic nucleus, and forebrain circumventricular organs, ventral tegmentum, the substantia nigra, pars compacta and reticulate.

In electrical stimulation mode, the implanted electrode is coupled to the signal generator of controller 10. As schematically shown in FIG. 3, for chemical/drug stimulation mode, a catheter connects the target tissue to a chemical/pharmaceutical delivery assembly (pump) that communicates with the controller 10. Leads 37,39 are preferably routed under the scalp to an implanted controller 10, however they could also be routed externally to an implanted or external controller. A catheter may also be similarly routed to an implanted or externally located pump. A catheter that also includes at least one electrode may also be employed, if desired.

A treatment regimen my employ a system which includes a sensing capability that is operated to detect electrical or chemical activity in a selected area of the brain or volume of neural tissue. Feedback of the detected neuronal activity is provided to the controller so that the stimulation signal (e.g., one or more parameters such as pulse current, pulse width, frequency, and on-time or off-time) is automatically adjusted, thereby enhancing treatment of the mood disorder. Preferred areas of the brain for sensing are insula, subcallosal area, cingulate, thalamus, prefrontal cortex, cerebellum, midbrain and brainstem, including the Brodmann areas or nuclei within those areas, and white matter tracts leading from any Brodmann area or nucleus. Preferably the sensing of a brain area is obtained epidurally, subdurally, or on the patient's scalp. Alternatively, at least one sensing electrode 26, or other sensing device, is placed in contact with, or in proximity to, one of the cranial nerves 27, as illustrated in FIG. 1 on the patient's left vagus in the neck. The selected cranial nerve is preferably one or more of the trigeminal, hypoglossal, vagus and accessory nerves. The nerve may be contacted at any point along its length or one of the nerve branches. For instance, stimulating or sensing electrodes may be located directly on, or proximal to, the left and/or right vagus nerve(s) in a near-diaphragmatic location (e.g., supra-diaphragmatic or sub-diaphragmatic).

After sufficient healing from the surgical implantation procedure has taken place the physician selects appropriate stimulation signals by actuating neurostimulation system 1 to generate electrical stimuli in the form of electrical impulses according to a programmed regimen for deep brain stimulation of the selected area of the patient's brain. During the electrode implantation procedure, the physician checks the current level of the pulsed signal to ascertain that the current is adjusted to a magnitude at least slightly below a threshold of the patient at which adverse effects would occur. Typically, the stimulation level is programmed such that the patient does not experience significant adverse effects attributable to the DBS therapy, although variations in device parameters settings may be observed from patient to patient. In any event, the maximum amplitude of the current should be adjusted accordingly until a beneficial effect (e.g., alleviation of mood disorders), with a suitable safety margin. The adverse effects and/or beneficial effects thresholds may change noticeably with time over a course of days after implantation, so the levels are preferably checked again in the first few days after implantation to determine whether any adjustment is necessary to maintain an effective regimen. The DBS regimen preferably employs an intermittent pattern of a period in which a repeating series of pulses is generated for stimulating the selected neural tissue in the brain, followed by a period in which no pulses are generated. The on/off duty cycle of these alternating periods of stimulation and no stimulation preferably has a ratio in which the off time is approximately 1.8 times the length of the on time. Preferably also, the width of each pulse is set to a value not greater than about 500 microseconds, and the pulse repetition frequency is programmed to be in a range of about 130 Hz. The above-described electrical and timing parameters of the stimulating signal used for DBS are merely exemplary and do not constitute a limitation of the scope of the present invention.

Figure 5:
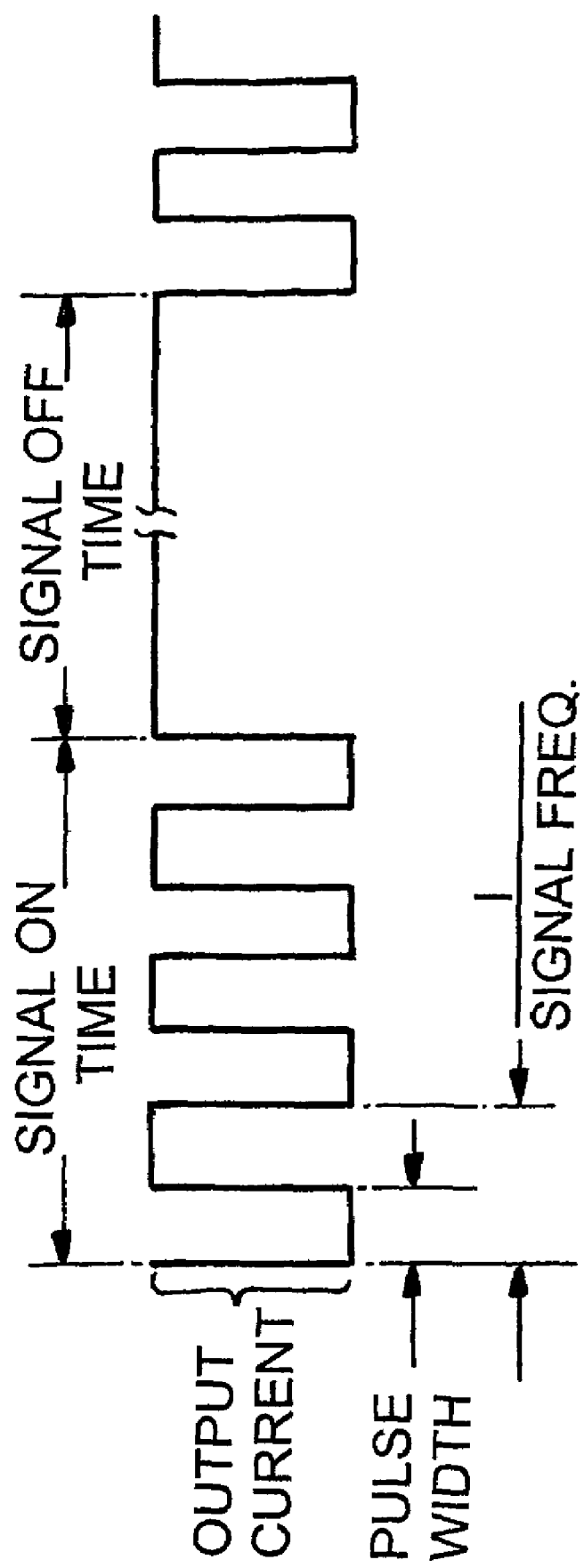
FIG. 5 is an illustrative idealized electrical output signal waveform of the signal generator useful for clarifying relevant parameters of the signal developed by the signal generator for application to the nerve, according to certain embodiments of the present invention.

As an aid to adjusting the programming of the system and optimizing the stimulating signal parameters for a particular patient's therapeutic regimen, a program of cranial nerve stimulation with selective deep brain sensing may be employed. This method includes placing an electrode in contact with, or in proximity to, one of the cranial nerves (preferably the left vagus nerve in the neck of the patient), and contacting a sensing electrode with a selected area of the patient's brain such as insula, subcallosal area, cingulate, thalamus, hypothalamus, prefrontal cerebral cortex, brain stem, cerebellum, and white matter tracts leading to or from an aforementioned area. Both electrodes are in communication with a controller/stimulus generator/processor unit, as described above. A predetermined electrical signal is applied to the cranial nerve electrode, causing stimulation or inhibition (modulation) of the electrical activity of the neural tissue that receives an electrical stimulus from that cranial nerve. An illustrative idealized electrical output signal waveform of the signal generator useful for clarifying relevant parameters of the signal developed by the signal generator for application to the nerve is shown in FIG. 5. The programming and settings of the controller/processor are adjusted to provide timing of bursts of electrical stimulation to the nerve, causing selective parasympathetic afferents of the cranial nerves to be stimulated, whereby one or more of the gustatory pathways, olfactory, pro-inflammatory or anti-inflammatory pathways, respiratory pathways, cardiac pathways, baroreceptor pathways, the somatosensory pathways, and satiety pathways are beneficially activated, causing a responsive attenuation of neural activity in various areas of the brain. Cranial nerve stimulation may also affect neurotransmitter pathways such as noradrenergic, serotoninergic, dopaminergic and cholinergic pathways similarly. The effect of such responsive effect on the brain tissue may be excitatory or inhibitory and may potentiate acute and/or long-term changes in neuronal activity. The responsive modulation or change in electrical activity of the neuronal tissue in the area of the patient's brain contacted by the implanted electrode is sensed and communicated to the controller 10. Alternatively, programming of the system and optimizing of the stimulating signal parameters for the patient's therapeutic regimen includes executing a program of selective DBS with selective deep brain sensing. For instance, a sensor is implanted in communication with a subcallosal area, and the system is then operated to sense electrical or chemical activity in the selected subcallosal area providing feedback to the controller to optimally adjust the stimulation for treating the patient's mood disorder. The stimulatory and sensed data is analyzed in the processor to determine any change in electrical activity of the selected brain area caused by application of a particular electrical signal. In this way, the signal parameters are adjusted under the supervision of the physician causing a responsive attenuation of neural activity in selective areas of the brain. Such modulation of electrical activity of the selected area of the brain is correlated by the processor with observed or expected alleviation of a symptom of the patient's mood disorder.

The patient's mood disorder symptoms should be allowed to stabilize at approximately the preoperative level before the DBS regimen is actually administered. Treatment applied in the form of chronic intermittent electrical stimulation over each twenty-four hour period may be observed initially to result in no change in mood disorder symptoms in the patient. But after a period of several days of this DBS regimen, a discernible improvement in symptoms of the mood disorder will occur. A typical result, in the case of depression, may be that debilitating feelings of sadness or hopelessness are lifted. The DBS treatment is not expected to adversely affect normal behavior in other aspects of the patient's life. A complete suspension of the DBS regimen would be expected to result in a relatively rapid return to the previous symptoms of depression or other mood disorder, ending after resumption of the DBS regimen. It is proposed that DBS stimulation of certain areas of the brain of individuals suffering from serious mood disorders may be a viable option for more effectively treating and changing unhealthy symptoms in persons suffering from serious depression, anxiety or other mood disorder which is not adequately treatable by existing therapies.

Selective Stimulation of an Insula Area. As indicated in FIG. 4A, a preferred treatment regimen comprises surgically implanting in the brain of a patient suffering from a serious mood disorder a stimulation lead having a proximal end and a stimulation portion, wherein after implantation the stimulation portion is in communication with a portion of the insula. The proximal end of the lead is coupled to a signal generator, which generates a predetermined electrical stimulation signal such that the signal electrically stimulates the selected insula area thereby modulating the neuronal activity of the affected tissue to ameliorate the mood disorder.

Selective Stimulation of a Subcallosal Area. In one treatment regimen, a predetermined stimulatory signal (e.g., electrical signal) is applied to a subcallosal area of the person's brain, and such stimulation of the selected subcallosal area produces modulation of neuronal activity in a subgenual cingulate area. By application of a different predetermined stimulatory signal, stimulation of the selected subcallosal area results in modulation of neuronal activity in the areas selected from the group consisting of Brodmann area 32, Brodmann area 25, Brodmann area 24, Brodmann area 10, and Brodmann area 9. As a result of such neuronal modulation of a selected subcallosal area, one or more symptoms of the mood disorder, or the frequency of repeated occurrences of the symptom is diminished. For instance, the stimulation portion (electrode) is in communication with Brodmann area 25, and an electrical signal stimulates Brodmann area 25 resulting in modulation of neuronal activity in Brodmann area 25, whereby the patient experiences a feeling of depression is diminished. Another treatment regimen comprises applying a predetermined electrical signal to Brodmann area 25 which results in modulation of neuronal activity in Brodmann area 9. Still another predetermined electrical signal is applied to Brodmann area 32, Brodmann area 25 which results in modulation of neuronal activity in Brodmann area 24 (FIG. 4B).

In chemical/pharmaceutical stimulation mode, the physician surgically implants a catheter having a proximal end in fluid communication with a pump and a discharge portion for infusing a dosage of a chemical or drug, such that after implantation the discharge portion of the catheter is in communication with a subcallosal area. Application of the predetermined stimulation signal comprises operating the pump to discharge the chemical/drug through the discharge portion of the catheter into the selected subcallosal area, thereby treating the mood disorder. Targeted neural tissue and the affected (modulated) neural tissue may be the same or different, depending on the selected chemical/pharmaceutical stimulation signal, similar to the above-described electrical stimulation mode. For instance, the protocol may include surgically implanting a catheter having a proximal end in fluid communication with a pump and a discharge portion for infusing a dosage of a pharmaceutical, wherein after implantation the discharge portion of the catheter is in communication with Brodmann 25 of the patient's brain. The predetermined stimulation signal is applied by operating the pump to discharge the pharmaceutical through the discharge portion of the catheter into Brodmann area 25 thereby modulating neural activity in that part of the brain to ameliorate symptoms of the mood disorder. Some applicable types of chemicals and/or pharmaceutical agents include inhibitory neurotransmitter agonists, excitatory neurotransmitter antagonists, agents that increases the level of an inhibitory neurotransmitter, agents that decrease the level of an excitatory neurotransmitter, and local anesthetic agents.

Selective Stimulation of the Intralaminar Nuclei. In another treatment a predetermined stimulatory signal (e.g., electrical signal) is applied to two or more subdivisions of the intralaminar nuclei which modulate separate cortical regions. The application of electrical stimulation may be synchronized when directed to two or more subdivisions of the intralaminar nuclei. As an alternative to electrical stimulation, another treatment arrangement employs a chemical dispensing device, as described above, so that a portion of the patient's intralaminar nuclei is contacted by a chemical agent (e.g., an excitatory neurotransmitter or an inhibitory neurotransmitter) to modulate neural activity in that part of the brain, resulting in amelioration of at least one symptom of the disorder.

Selective Stimulation of a Subgenual Cingulate Area. Another preferred treatment regimen comprises surgically implanting an electrical stimulation lead having a proximal end and a stimulation portion, wherein after implantation the stimulation portion is in communication with a subgenual cingulate area. The proximal end of the lead is coupled to a signal generator that generates a predetermined electrical stimulation signal whereby the signal electrically stimulates the subgenual cingulate area to modulate the neuronal activity of the affected tissue which, in turn, ameliorates the mood disorder.

Selective Bimodal Stimulation—Electrical/Chemical DBS. Another treatment regimen includes both electrical and chemical stimulation modes. The physician surgically implants an electrical stimulation lead having a proximal end and a stimulation portion, wherein after implantation the stimulation portion is in communication with a subcallosal area of the person's brain. The physician also surgically implants a catheter having a proximal end in fluid communication with a pump and a discharge portion for infusing a dosage of a chemical or a pharmaceutical agent, such that after implantation the discharge portion of the catheter is in communication with the selected subcallosal area. The proximal end of the lead is coupled to a signal generator, and a predetermined electrical signal is generated by the signal generator such that the selected subcallosal area is stimulated. Additionally, the pump is operated to discharge the chemical or pharmaceutical agent through the discharge portion of the catheter into a selected subcallosal area such that a subcallosal area is additionally stimulated by the chemical or pharmaceutical agent, to enhance alleviation of the mood disorder.

One procedure in which DBS and cranial nerve stimulation are employed together includes coupling a first electrode to a selected area of the patient's brain that is known or expected to be associated with mood disorder symptoms (e.g., insula, subcallosal area, cingulate, thalamus, prefrontal cerebral cortex, brain stem, cerebellum, including Brodmann areas or nuclei therein, and white matter tracts leading to one or more of such Brodmann areas or nuclei). A second electrode is coupled to a cranial nerve of the patient. A predetermined therapeutic electrical signal is applied to the first electrode, to stimulate the neural tissue, and a second predetermined therapeutic electrical signal is applied to the second electrode. As a result of the dual application of the first and second signals, advantageous modulation of the neuronal activity of the selected area of neural tissue is obtained which ameliorates depression, anxiety or other mood disorder.

Another bimodal stimulation regimen comprises surgically implanting a stimulator electrode in direct or indirect communication with Brodmann 25. A catheter, having a proximal end in fluid communication with a pump and a discharge portion for infusing a dosage of a pharmaceutical, is surgically implanted such that the discharge portion of the catheter is also in communication with Brodmann area 25. A predetermined electrical signal is applied to the electrode such that the Brodmann area 25 is stimulated. Additionally, the pump is operated to discharge the pharmaceutical agent through the discharge portion of the catheter into Brodmann area 25 such that Brodmann 25 is additionally stimulated, to enhance alleviation of the disorder. Electrical and chemical stimulation may be applied simultaneously or sequentially, as determined by the physician.

Selective DBS with Feedback Sensing. When a sensing capability is included, the implantable or external processor is additionally configured for measuring, sensing, recording, monitoring the physiological activity, physiological event, physiological threshold, body or brain state. This is accomplished, for instance, by sensing electrical activity in the nerve (action potentials), in or from the brain, heart, gastrointestinal tract, pancreas or other organs innervated by the vagus nerve. The processor and controller are configured such that the treatment parameters can be varied or adjusted based on adaptive learning, whereby the system detects activity or physiologic changes after stimulation and automatically adjusts the controller to attempt to deliver optimized therapy. The controller/processor can also determine the result of adverse stimulation and adjust the stimulation to prevent an adverse patient response.

An adaptive brain stimulation system is employed for treating a patient suffering from depression, anxiety, or other mood disorder by stimulating a first brain region or a first set of brain regions in the patient according to a defined set of stimulation parameters which are derived according to a procedure that includes sensing a present state of the patient, and then comparing the resulting data related to the sensed present state of the patient to data related to a reference state, and obtaining comparison results. From those results, it is determined whether to make a change in the stimulation parameters, and if so, what change is to be made, depending on the comparison results. The attending physician then makes the appropriate changes in the stimulation parameters, as determined by the aforementioned comparison of present and reference states. The sensing, comparing, determining and adjusting steps are repeated any number of times, as deemed necessary. Stimulation of a second brain region or a second set of brain regions of the patient may also be carried out, depending on the comparison results. Preferably, stimulation of a second brain region or set of brain regions causes a positive reinforcement (e.g., a decrease in severity or occurrence of mood disorder symptoms). The step of sensing a present state of the patient may comprise sensing a state of one or more peripheral regions of the patient's body. The changes that are made to the stimulation signal may comprise adjusting parameters so as to stimulate selective parasympathetic afferents of the cranial nerves to activate the gustatory pathways, olfactory, pro-inflammatory or anti-inflammatory pathways, respiratory pathways, cardiac pathways, baroreceptor pathways, the somatosensory pathways, and satiety pathways. Cranial nerve stimulation may also affect neurotransmitter pathways such as noradrenergic, serotoninergic, dopaminergic and cholinergic pathways similarly.

Cranial Nerve Stimulation with Selective Deep Brain Sensing. In a variation of the foregoing bimodal stimulation method, cranial nerve stimulation is employed instead of, or in addition to, deep brain stimulation (DBS). In this variation of the method, one of the cranial nerves is electrically stimulated instead of electrically stimulating a subcallosal area. At least one stimulation electrode or chemical/drug stimulation assembly is placed in contact with, or in proximity to, one of the cranial nerves The selected cranial nerve is preferably the trigeminal, hypoglossal, vagus or accessory nerve. The nerve may be contacted at any point along its length or one of the nerve branches. For instance, as illustrated in FIG. 1, electrode 26 is preferably a bipolar stimulating electrode, preferably of the helical type described in U.S. Pat. No. 4,573,481 (Bullara). The electrode assembly is surgically implanted on the vagus nerve 27 in the patient's neck. Alternatively, the physician may surgically implant a pair of stimulation electrodes on the left and right vagus nerve and the stimulation signal parameters are adjusted to bilaterally stimulate both vagus nerves, in synchrony or asynchronously, in order to selectively inhibit, excite, or block selective areas of the brain to alleviate depressive symptoms. The controller/processor is adjusted to provide timing of bursts of electrical bilateral stimulation to attenuate the neural activity in selective areas of the brain to achieve the desired result. The signal parameters may be adjusted so as to stimulate selective parasympathetic afferents of the cranial nerves, whereby one or more of the gustatory pathways, olfactory, pro-inflammatory or anti-inflammatory pathways, respiratory pathways, cardiac pathways, baroreceptor pathways, the somatosensory pathways, and satiety pathways are beneficially activated. Similarly, cranial nerve stimulation may affect neurotransmitter pathways such as noradrenergic, serotoninergic, dopaminergic and cholinergic pathways.

A cranial nerve stimulation configuration is especially useful for optimizing the stimulating signal parameters, as mentioned above. For instance, as illustrated in FIG. 1, an electrode 26 is coupled to a cranial nerve (e.g., the vagus, hypoglossal, trigeminal or accessory nerve) of the individual, and communicates with controller 10 via lead 22. Another electrode 38, a sensing electrode or "sensor," is coupled to a selected area of the patient's brain such as insula, subcallosal area, cingulate, thalamus, prefrontal cerebral cortex, brain stem, cerebellum, or a white matter tracts leading from an aforementioned area or from a Brodmann area or nucleus therein. Electrode 38 is also in communication with a controller/stimulus generator/processor unit. A predetermined electrical signal is applied to the cranial nerve electrode, causing stimulation or inhibition (modulation) of the electrical activity of the neural tissue that receives an electrical stimulus from that cranial nerve. The responsive modulation or change in electrical activity of the neuronal tissue is sensed by the implanted electrode and communicated to the controller/processor 10. The data is analyzed in the processor to determine whether application of a particular electrical signal causes a change in electrical activity of the selected brain area. Such modulation of electrical activity of the selected area is also correlated by the processor with subjective or objective data indicating alleviation of a symptom of a mood disorder.

Combined DBS and VNS. One procedure in which deep brain stimulation (DBS) and cranial nerve stimulation (VNS) are employed together includes coupling a first electrode to a cranial nerve of the patient. FIG. 1 illustrates an electrode coupled to a patient's left vagus nerve in the neck. A second electrode is coupled to a selected area of the patient's brain that is known or expected to be associated with symptoms of a particular mood disorder (e.g., a subcallosal area). A predetermined therapeutic electrical signal is applied to the first electrode, to stimulate the cranial nerve, and a second predetermined therapeutic electrical signal is applied to the second electrode to stimulate the neural tissue. As a result of the dual application of the first and second signals, advantageous modulation of the neuronal activity of the selected area of neural tissue is obtained which ameliorates depression, anxiety, or another mood disorder. In an alternative treatment configuration, the stimulation parameters may be adjusted to bilaterally stimulate both vagus nerves, for instance, in synchrony or asynchronously, in order to selectively inhibit, excite, or block selective areas of the brain to provide the desired alleviation of symptoms of the mood disorder. The controller may be adjusted to provide timing of bursts of bilateral electrical stimulation to cause attenuation of neural activity in selective areas of the brain.

Combined DBS/VNS—Bimodal Electrical/Chemical Stimulation

Another representative combined DBS/VNS treatment includes surgically implanting an electrode and lead assembly having a proximal end and a stimulation portion, wherein after implantation the stimulation portion (i.e., electrode) is in communication with either a cranial nerve or a subcallosal area. The physician also surgically implants a catheter having a proximal end in fluid communication with a pump and a discharge portion for infusing a dosage of a chemical agent. After implantation the discharge portion of the catheter is in communication with a subcallosal area. The physician couples the proximal end of the lead to a signal generator. An appropriate electrical signal is created using the signal generator and is applied via the electrode and lead assembly, causing the signal to electrically stimulate the selected subcallosal area. In concert with the electrical stimulation, the pump operates to discharge the chemical agent through the discharge portion of the catheter into the same or a different subcallosal area, thereby treating the mood and/or anxiety disorder.

Similarly, the physician may surgically implant an electrode/lead assembly such that, after implantation, the stimulation portion is in communication with Brodmann area 25. Likewise, the discharge portion of the catheter is also located in communication with Brodmann area 25. The electrical signal electrically stimulates Brodmann area 25 while the pump discharges the chemical agent into Brodmann area 25, to provide a combined, bi-modal therapeutic treatment for the mood and/or anxiety disorder.

Triggered activation/deactivation. Preferably the desired stimulation, and resulting modulation, can be triggered by sensing of a predetermined event or condition or by manual activation from an external device, or from physician input or from patient input. If an above-described manual activation switch is included on the implantable controller, and should the physician determine that it is appropriate for the patient to have limited control over the device, the programming of the processor is adjusted to allow the signal generator to emit a predetermined stimulation signal upon detection by the controller of the requisite manual input from the patient.

Magnetic stimulation. As an alternative to surgical implantation of a DBS stimulator, an area of the brain such as the orbitofrontal cortex may instead be stimulated via transcranial magnetic stimulation. Thus, the stimulus can be electrical, chemical/drug, or magnetic, or a combination of any of those modes.

Combined Therapies for Treating Mood Disorders

An above-described stimulation regimen may be combined with a conventional drug therapy, if deemed appropriate by the physician. For instance, a conventional antidepressant could be administered to the patient during the course of DBS treatment for depression or other serious mood disorder. Some conventional antidepressants include tricyclic antidepressants and analogs thereof, serotonin reuptake inhibitors, serotonin-norepinephrine reuptake inhibitors, norepinephrine reuptake inhibitors, dopamine reuptake inhibitors, norepinephrine-dopamine reuptake inhibitors, serotonin-norepinephrine-dopamine reuptake inhibitors, serotonin reuptake accelerators, serotonin agonists and prodrugs thereof, and monoamine oxidase inhibitors. Tricyclic antidepressants, and their and analogs, include amineptine, amitriptyline, clomipramine, desipramine, doxepin, dothiepin, imipramine, nortriptyline, protriptyline, trimipramine, amoxapine, maprotiline, and cyclobenzaprine, for example. Serotonin reuptake inhibitors include the selective serotonin reuptake inhibitors citalopram, escitalopram, fluoxetine, fluvoxamine, paroxetine, and sertraline, for example. Serotonin-norepinephrine reuptake inhibitors may include milnacipran, mirtazapine, venlafaxine, duloxetine, S33005, DVS-233 (desvenlafaxine), DVS-233 SR and sibutramine, for example. Norepinephrine reuptake inhibitors include the selective norepinephrine reuptake inhibitors reboxetine and atomoxetine. Norepinephrine-dopamine reuptake inhibitors include amineptine, bupropion, and GW353162, for example. Monoamine oxidase inhibitors include befloxatone, brofaromine, deprenyl, isocarboxazid, moclobemide, pargyline, phenelzine, selegiline, and tranylcypromine, for example.

Additionally, or alternatively, one or more of these drugs may be dispensed at an above-mentioned location in the brain via an implantable drug delivery device, if desired.

The above-described methods are believed to be useful to physicians in formulating appropriate therapeutic treatment of patients who suffer from serious mood disorders.

Without further elaboration, it is believed that one skilled in the art can, using the description herein, utilize the present invention to its fullest extent. The foregoing embodiments are to be construed as illustrative, and not as constraining the remainder of the disclosure in any way whatsoever. While the preferred embodiments of the invention have been shown and described, modifications thereof can be made by one skilled in the art without departing from the spirit and teachings of the invention. For instance, it should be understood that the various stimulation, sensing and activation modes, programmable features, and the like, that are described herein may be rearranged or employed in different combinations than those expressly exemplified. Many variations and modifications of the embodiments disclosed herein are possible and are within the scope of the invention. Accordingly, the scope of protection is not limited by the description set out above, but is only limited by the claims which follow, that scope including all equivalents of the subject matter of the claims. The disclosures of all patents, patent applications and publications cited herein are hereby incorporated herein by reference, to the extent that they provide exemplary, procedural or other details supplementary to those set forth herein.

What is claimed is:

1. A method of treating an individual suffering from a mood disorder, the method comprising:
   coupling a first stimulator to a stimulation site comprising a volume of neural tissue in an area of the individual's brain selected from the group consisting of insula, subcallosal area, cingulate, thalamus, prefrontal cerebral cortex, brain stem, cerebellum, and white matter tracts leading to or from an aforementioned area;
   coupling a second stimulator to a cranial nerve of the individual;
   applying a first stimulation signal to said first stimulator such that said first stimulation signal causes modulation of the neuronal activity of neural tissue in said selected area of the brain;
   applying a second stimulation signal to said second stimulator such that said second stimulation signal causes modulation of the neuronal activity in said cranial nerve, wherein said modulations cause amelioration of the mood disorder.

2. The method of claim 1 wherein said second stimulation signal causes selective parasympathetic afferents of the cranial nerves to be stimulated, whereby at least one cranial nerve pathway is affected causing a responsive effect on neural activity in at least one area of the brain to enhance amelioration of the mood disorder.

3. The method of claim 2 wherein said cranial nerve pathway is chosen from the group consisting of gustatory pathways, olfactory, pro-inflammatory or anti-inflammatory pathways, respiratory pathways, cardiac pathways, baroreceptor pathways, the somatosensory pathways, satiety pathways, and noradrenergic, serotoninergic, dopaminergic and cholinergic neurotransmitter pathways.

4. The method of claim 3 wherein said responsive effect on said area of the brain is excitatory or inhibitory and potentiates acute and/or long-term changes in neuronal activity of said area of the brain.

5. The method of claim 1 wherein said first and/or second stimulation signal causes modulation of neuronal activity in a neural tissue of said individual other than said area coupled to said first stimulator.

6. The method of claim 1 wherein said first stimulation signal comprises a first acute stimulation component and a first chronic stimulation component and/or said second stimulation signal comprises a second acute stimulation component and a second chronic stimulation component.

7. The method of claim 6 wherein said first acute stimulation component comprises a higher intensity level of stimulation and shorter duration than said first chronic stimulation component and/or said second acute stimulation component comprises a higher intensity level of stimulation and shorter duration than said second chronic stimulation component.

8. The method of claim 6 wherein said first and/or second acute stimulation component comprises a duration of one to six months.

9. The method of claim 1 wherein said cranial nerve is selected from the group consisting of vagus, trigeminal, hypoglossal and accessory nerves.

10. The method of claim 1 wherein said first stimulator is a first electrode and said second stimulator is a second electrode, and said method further comprises: providing at least one programmable electrical signal generator coupled to said first and second electrodes; programming said at least one electrical signal generator to define each of said first and second stimulation signals by a plurality of electrical parameters comprising a current magnitude, a pulse frequency, and a pulse width, wherein said parameters are selected to alleviate a symptom of said mood disorder.

11. The method of claim 1 wherein said first and/or second stimulator comprises at least one chemical dispensing assembly comprising a chemical-filled reservoir and a catheter in communication with a pump, said catheter comprising a dispensing end located on or near said nerve or brain area, and said first and/or second stimulation signal each comprises a therapeutic pumping signal, said method comprising: operating at least one said pump such that said chemical contacts said cranial nerve and/or said brain area, whereby the neuronal activity of the contacted nerve and/or brain area is modified, and such modification of neuronal activity causes alleviation of a symptom of the mood disorder.

12. The method of claim 11 wherein said chemical agent is selected from the group consisting of inhibitory neurotransmitter agonists, excitatory neurotransmitter antagonists, agents that increase the level of an inhibitory neurotransmitter, agents that decrease the level of an excitatory neurotransmitter, and local anesthetic agents.

13. The method of claim 1 wherein said area comprises the insula or a white matter tract leading to a portion of the insula.

14. The method of claim 13 wherein said area comprises the left anterior insula, the left posterior insula, the right anterior insula, the left posterior insula, the claustrum, or a white matter tract leading to an aforementioned area.

15. The method of claim 1 wherein said area comprises at least a portion of the cingulate or a white matter tract leading to a portion of the cingulate.

16. The method of claim 1 wherein said area comprises at least a portion of a subcallosal area or a white matter tract leading to a portion of a subcallosal area.

17. The method of claim 1 wherein said area comprises at least a portion of a Brodmann area chosen from the group consisting of Brodmann area 24, Brodmann area 25 and Brodmann area 32.

18. The method of claim 1 wherein said area comprises at least a portion of the prefrontal cortex or a white matter tract leading to a portion of the prefrontal cortex.

19. The method of claim 18 wherein said area comprises the orbitofrontal cortex or a Brodmann area chosen from the group consisting of Brodmann area 8, Brodmann area 9, Brodmann area 10 and Brodmann area 11, or a white matter tract leading to the orbitofrontal cortex or an aforementioned Brodmann area.

20. The method of claim 1 wherein said area comprises at least a portion of the thalamus or a white matter tract leading to a portion of the thalamus.

21. The method of claim 1 wherein said area comprises a parafascicular nucleus or a white matter tract leading to a parafascicular nucleus.

22. The method of claim 1 wherein said area comprises at least a portion of the cerebellum, midbrain, or brainstem, or a white matter tract leading to a nucleus therein.

23. A method of treating an individual suffering from a mood disorder, the method comprising:
 providing a controller comprising a signal generator and processor in communication with a first electrode and a second electrode;
 coupling said first electrode to a cranial nerve of the individual;
 coupling said second electrode to a volume of neural tissue in an area of the individual's brain selected from the group consisting of insula, subcallosal area, cingulate, thalamus, hypothalamus, prefrontal cerebral cortex, brain stem, cerebellum, and white mailer tracts leading from an aforementioned area;
 applying a predetermined electrical signal to said first electrode; and
 sensing electrical activity in said selected volume of brain tissue by said second electrode; comparing the resulting sensed electrical activity to a predetermined electrical state of said selected area; and
 determining from said comparison whether said application of said predetermined electrical signal to said first electrode causes a modulation of electrical activity of said brain area, wherein said modulation of electrical activity corresponds to alleviation of a symptom of a mood disorder.

24. The method of claim 23 wherein said cranial nerve is selected from the group consisting of vagus, trigeminal, hypoglossal and accessory nerves.

25. The method of claim 23 further comprising adjusting said predetermined signal according to said comparison results, to alter said modulation of neuronal activity in said selected brain area to enhance alleviation of a symptom of said mood disorder.

26. An adaptive brain stimulation process for treating a patient suffering from a mood disorder, the process comprising:
 (a) providing a system comprising at least one sensor for coupling with a status indicator site on the patient to sense a present state of at least a first brain region or set of brain regions;
 a first stimulating circuit for coupling at least said first brain region or set of brain regions by at least one stimulation electrode, to carry out stimulation according to a first set of stimulation parameters;
 a comparator adapted for coupling with said at least one sensor, said comparator adapted for receiving data related to the present state and comparing said present state data with reference state data, such that said comparing results in a positive outcome or a negative outcome; and at least one control circuit coupled with at least said first stimulating circuit and adapted for being adjusted according to the outcome of said comparing of said present and reference states, to control said stimulation parameters;

(b) coupling said at least one sensor with said a status indicator site on the patient;

(c) stimulating at least a first brain region or a first set of brain regions of the patient according to a first set of stimulation parameters;

(d) sensing a present state of said patient to provide sensed data;

(e) comparing said sensed data with reference state data to derive comparison results;

(f) determining from said comparison results whether a change in the stimulation parameters is necessary;

(g) if said change is necessary, determining what changes are to be made in said stimulation parameters;

(h) changing said first set of stimulation parameters as determined in step (f); and (i) repeating steps (c)-(h) with the resulting changed stimulation parameters, until no further change is determined to be necessary in step (g).

27. The process of claim 26 further comprising stimulating a second brain region or a second set of brain regions of the patient if the comparison results indicate that a response signal causes a therapeutic benefit.

28. The process of claim 27 wherein said step of stimulating a second brain region or a second set of brain regions causes a beneficial therapeutic effect.

29. The a process of claim 26 wherein step (d) comprises sensing neuronal activity of a peripheral cranial nerve.

30. The process of claim 26 wherein, in step (g), changing said stimulation parameters comprises providing a stimulation signal that stimulates selective parasympathetic afferents of the cranial nerves to activate at least one cranial nerve pathway chosen from the group consisting of the gustatory pathways, olfactory, pro-inflammatory or anti-inflammatory pathways, respiratory pathways, cardiac pathways, baroreceptor pathways, the somatosensory pathways, satiety pathways, and noradrenergic, serotoninergic, dopaminergic and cholinergic neurotransmitter pathways.

* * * * *